US010934247B2

(12) United States Patent
Smith et al.

(10) Patent No.: US 10,934,247 B2
(45) Date of Patent: *Mar. 2, 2021

(54) NITROGEN AND/OR OXYGEN-CONTAINING HYDROFLUOROOLEFINS AND METHODS OF MAKING AND USING THE SAME

(71) Applicant: 3M INNOVATIVE PROPERTIES COMPANY, St. Paul, MN (US)

(72) Inventors: Sean M. Smith, Woodbury, MN (US); Michael J. Bulinski, Stillwater, MN (US); Michael G. Costello, Afton, MN (US); William M. Lamanna, Stillwater, MN (US); Nicholas A. Toso, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/323,623

(22) PCT Filed: Aug. 8, 2017

(86) PCT No.: PCT/US2017/045834
§ 371 (c)(1),
(2) Date: Feb. 6, 2019

(87) PCT Pub. No.: WO2018/057134
PCT Pub. Date: Mar. 29, 2018

(65) Prior Publication Data
US 2020/0071258 A1    Mar. 5, 2020

Related U.S. Application Data

(60) Provisional application No. 62/399,537, filed on Sep. 26, 2016.

(51) Int. Cl.
*C07C 211/24*    (2006.01)
*C07C 41/28*    (2006.01)
(Continued)

(52) U.S. Cl.
CPC ............ *C07C 211/24* (2013.01); *C07C 41/28* (2013.01); *C07C 41/30* (2013.01); *C07C 43/17* (2013.01);
(Continued)

(58) Field of Classification Search
CPC ....... C07C 211/24; C07C 41/28; C07C 41/30; C07C 43/17; C07C 67/42; C07C 209/70; C07C 209/78; C07C 227/02; C07C 29/44; C07C 67/08; C07C 41/18; H01M 10/0567; H01M 10/0569; H01M 2300/0034;
(Continued)

(56) References Cited

U.S. PATENT DOCUMENTS 4,782,148 A    11/1988 Abe
4,985,556 A    1/1991 Abe
(Continued)

FOREIGN PATENT DOCUMENTS

EP    1535892    6/2005
JP    01070445    3/1989
(Continued)

OTHER PUBLICATIONS

CAS reg. No. 2215952-96-6, Apr. 19, 2018. (Year: 2018).*
PALETA_"Experimental Evidence for a Free-Radical Chain Mechanism in the Photo-Initiated Audition of Alcohols," Tetrahedron Letters, vol. 32, pp. 252-254, 1991.
Abe, "A new route to Perfluorovinylamines by the Pyrolytic Reaction of an Alkali Metal Salt of Perfluoro (2-dialkylamino-propionic acids)", The chemical Society of Japan, 1988, pp. 1887-1890.
Abe, An alternative new route to perfluorovinylamines. Pyrolysis of an alakiali metal salt of perfluoro (3-dialkylamino-proponic acids), The chemical society of Japan, 1989, pp. 905-908.
Abe, "The electrochemical fluorination of nitrogen-containing carboxylic acids. Fluorination of dimethylamino- or diethylamino-substituted carboxylic acid derviatives", Journal of fluorine chemistry, 1990, vol. 48, pp. 257-279.
Abe, "The electrochemical fluorination of nitrogen-containing carboxylic acids*. Flurination of methyl esters of cyclic amino-group substituted carboxylic acids", Journal of fluorine chemistry, 1990, vol. 50, pp. 173-196.
Bailey, Pyrolysis of esters. VII. Influence of aci portion[1,2], 1957, J. Org. Chem., vol. 21, pp. 543-545.
Bailey, "Pyrolysis of Esters. XV. Effect of temperature on direction of elimination of tertiary esters", 1959, vol. 81, pp. 647-651.
(Continued)

*Primary Examiner* — Douglas J McGinty
(74) *Attorney, Agent, or Firm* — Julie Lapos-Kuchar

(57) ABSTRACT

The present invention relates to an unsaturated fluorinated ether or amine compound of formula (I) with low global warming potential and method of making the compound (I), where $R_H^1$ is and $R_H^2$ are independently selected from H or $CH_3$, wherein when $R_H^1$ is $CH_3$ then $R_H^2$ is H and when $R_H^2$ is $CH_3$, then $R_H^1$ is H; X is O or N and when X is O, then n is 1 and $R_f$ is a linear or branched perfluorinated alkyl group comprising 1-10 carbon atoms and optionally comprising at least one catenated O or N atom; X is N, then n is 2 and (i) each $R_f$ is independently selected from a linear or branched perfluorinated alkyl group comprising 1-8 carbon atoms and optionally comprising at least one catenated O or N atom, or (ii) the two $R_f$'s are bonded together to form a ring structure optionally comprising at least one catenated O or N atom, wherein the ring of the ring structure consists of 5-7 atoms, no more than 10 carbon atoms, and is perfluorinated. The applications of the compound include solvent cleaning, electrolyte solvents or additives, heat transfer, and vapour phase soldering.

20 Claims, No Drawings

(51) Int. Cl.

| | | |
|---|---|---|
| *C07C 41/30* | (2006.01) | |
| *C07C 43/17* | (2006.01) | |
| *C07C 67/42* | (2006.01) | |
| *C07C 209/70* | (2006.01) | |
| *C07C 209/78* | (2006.01) | |
| *C07C 227/02* | (2006.01) | |
| *C07D 295/067* | (2006.01) | |
| *C09K 5/10* | (2006.01) | |
| *C11D 3/24* | (2006.01) | |
| *C11D 3/43* | (2006.01) | |
| *C23G 5/028* | (2006.01) | |
| *H01M 10/0567* | (2010.01) | |
| *H01M 10/0569* | (2010.01) | |

(52) U.S. Cl.
CPC .......... *C07C 67/42* (2013.01); *C07C 209/70* (2013.01); *C07C 209/78* (2013.01); *C07C 227/02* (2013.01); *C07D 295/067* (2013.01); *C09K 5/10* (2013.01); *C11D 3/245* (2013.01); *C11D 3/43* (2013.01); *C23G 5/02803* (2013.01); *H01M 10/0567* (2013.01); *H01M 10/0569* (2013.01); *H01M 2300/0034* (2013.01)

(58) Field of Classification Search
CPC .... D06L 1/04; C10M 105/58; C23G 5/02883; C23G 5/0289; C23G 5/032; C23G 5/036; C23G 5/028; C23G 5/02803; C07D 265/30; C07D 207/10; C07D 295/067; C07D 223/06; C07D 241/04; C07D 211/38; C11D 3/24; C11D 7/50; C11D 3/245; C11D 3/43; C09K 5/00; C09K 5/10
USPC ............................................ 252/67, 68, 69
See application file for complete search history.

(56) References Cited

U.S. PATENT DOCUMENTS

| | | | |
|---|---|---|---|
| 6,203,944 B1 | 3/2001 | Turner | |
| 6,255,017 B1 | 7/2001 | Turner | |
| 10,266,472 B2* | 4/2019 | Bulinski | C08J 9/12 |
| 10,344,006 B2* | 7/2019 | Smith | C11D 3/245 |
| 10,577,335 B2* | 3/2020 | Smith | C07C 43/17 |
| 2010/0139274 A1 | 6/2010 | Zyhowski | |
| 2016/0145195 A1 | 5/2016 | Bulinski | |
| 2016/0312096 A1* | 10/2016 | Bulinski | A62D 1/0092 |
| 2018/0141893 A1* | 5/2018 | Lamanna | C07C 211/24 |
| 2018/0312478 A1* | 11/2018 | Smith | C07D 241/04 |
| 2018/0319908 A1* | 11/2018 | Bulinski | C09D 127/18 |
| 2019/0031646 A1* | 1/2019 | Smith | C07D 307/14 |
| 2019/0040024 A1* | 2/2019 | Smith | C11D 7/28 |
| 2019/0185402 A1* | 6/2019 | Smith | C09K 5/10 |
| 2020/0190071 A1* | 6/2020 | Teverovskiy | C11D 7/3281 |
| 2020/0207727 A1* | 7/2020 | Smith | C07C 231/14 |

FOREIGN PATENT DOCUMENTS

| | | |
|---|---|---|
| WO | WO 2016-064585 | 4/2016 |
| WO | WO 2016-196240 | 12/2016 |
| WO | WO 2016-196242 | 12/2016 |
| WO | WO 2017-095732 | 6/2017 |
| WO | WO 2017-195070 | 11/2017 |

OTHER PUBLICATIONS

Depuy, "Pyrolytic cis eliminations", R.W.Chem Rev, 1960, vol. 60, pp. 431-457.
Ellis, "Cleaning and contamination of electronics components and assemblies" Electrochemical Publications Limited, 1986, Scotland, pp. 182-196.
Froemsdorf, "The direction of elimination in the pyrolysis of acetates", J. Am. Chem.Soc., 1959, vol. 81, pp. 643-647.
Kaneko, "A New Synthetic Route to Perfluoroacrylic Acid," Reports of the Research Laboratory, Asahi Glass Co., Ltd., vol. 36, 1986, pp. 243-248.
Krespan, "Perfluoroallyl fluorosulfate, a reactive new perfluoroallylating agent", J. Am. Chem. Soc., 1981, vol. 103, pp. 5598-5599.
Wlassics, "Perfluoro allyl fluorosulfate (FAFS): A versatile building block for new fluoroallylic compounds", 2011, vol. 16, pp. 6512-6540.
International Search report for PCT International Application No. PCT/US2017/045834 dated Nov. 15, 2016, 5 pages.

* cited by examiner

NITROGEN AND/OR OXYGEN-CONTAINING HYDROFLUOROOLEFINS AND METHODS OF MAKING AND USING THE SAME

CROSS REFERENCE TO RELATED APPLICATIONS

This application is a national stage filing under 35 U.S.C. 371 of PCT/US2017/045834, filed Aug. 8, 2017, which claims the benefit of U.S. Application No. 62/399,537, filed Sep. 26, 2016, the disclosure of which is incorporated by reference in its/their entirety herein.

TECHNICAL FIELD

The present disclosure relates to unsaturated hydrofluorinated compounds comprising an amine and/or ether moiety and methods of making and using the same.

SUMMARY

There continues to be a need for inert fluorinated fluids which have low global warming potential while providing high thermal stability, low toxicity, nonflammability, good solvency, and a wide operating temperature range to meet the requirements of various applications. Those applications include, but are not restricted to, heat transfer, solvent cleaning, fire extinguishing agents, and electrolyte solvents and additives. The fluorinated fluids used in these applications are typically saturated hydrofluoroethers, saturated hydrofluorocarbons, and saturated perfluorocarbons. The fluorinated compounds described herein are unsaturated and comprise an amine and/or ether group. The compounds described herein offer some of the same physical properties as the above-mentioned fluorinated fluids, but generally provide lower atmospheric lifetimes and global warming potentials to provide a more acceptable environmental profile.

In one aspect, an unsaturated fluorinated compound of formula (I) is discussed

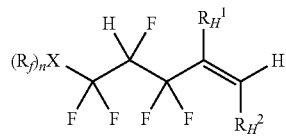

where
$R_H^1$ is and $R_H^2$ are independently selected from H or $CH_3$, wherein when $R_H^1$ is $CH_3$ than $R_H^2$ is H and when $R_H^2$ is $CH_3$ than $R_H^1$ is H;
X is O or N and when
X is O, then n is 1 and $R_f$ is a linear or branched perfluorinated alkyl group comprising 1-10 carbon atoms and optionally comprising at least one catenated O or N atom;
X is N, then n is 2 and (i) each $R_f$ is independently selected from a linear or branched perfluorinated alkyl group comprising 1-8 carbon atoms and optionally comprising at least one catenated O or N atom, or (ii) the two $R_f$'s are bonded together to form a perfluorinated ring structure comprising no more than 10 carbon atoms and optionally comprising at least one catenated O or N atom, wherein the ring of the ring structure consists of 5-7 atoms.

In another aspect, a method of making an unsaturated fluorinated compound is described. The method comprising:

(i) reacting a perfluorinated allylic compound with a first alcohol in the presence of a free radical initiator to form a second alcohol, wherein the perfluorinated allylic compound comprises a perfluorinated allylic ether or a perfluorinated allylic amine, the first alcohol is a primary alcohol or a secondary alcohol, and the second alcohol is a secondary or tertiary fluorinated alcohol;

(ii) acylating the second alcohol to form a fluorinated ester; and (iii) vapor phase dehydroacetoxylating the fluorinated ester to form the unsaturated fluorinated compound.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more; and
"and/or" is used to indicate one or both stated cases may occur, for example A and/or B includes, (A and B) and (A or B);
"catenated" means an atom other than carbon (for example, oxygen or nitrogen) that is bonded to at least two carbon atoms in a carbon chain (linear or branched or within a ring) so as to form a carbon-heteroatom-carbon linkage;
"perfluorinated" means a group or a compound wherein all hydrogen atoms in the C—H bonds have been replaced by C—F bonds;
"saturated" refers to a compound having no carbon-carbon double bonds or triple bonds;
"unsaturated" refers to a compound having at least one carbon-carbon double bond; and
"substituted" (in reference to a group or moiety) means that at least one carbon-bonded hydrogen atom is replaced with a halogen atom. Halogen atoms may include F, Cl, Br, and I.

As used herein, a chemical structure that depicts the letter "F" in the center of a ring indicates that all unmarked bonds of the ring are fluorine atoms.

It should be understood, that although not shown, there are hydrogen atoms bonded to the carbon atoms of the cyclic ring to complete the valency of the individual carbon atoms, as is common nomenclature. It should also be understood, that although not shown, there are hydrogen atoms bonded to the carbon atoms of the structures to complete the valency of the individual carbon atoms, as is common nomenclature.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

Because of their properties, such as inertness, good solvency, and high thermal stability; fluorinated fluids such as saturated hydrofluoroethers, saturated hydrofluorocarbons, saturated perfluorocarbons, and saturated hydrochlorofluorocarbons have been used in heat transfer, solvent cleaning, fire extinguishing, and electrolyte applications. In view of an increasing demand for environmentally-friendly chemical compounds, it is recognized that there exists an ongoing need for new fluids that provide reductions in environmental impact, and which can meet the performance requirements (e.g., nonflammability, solvency, and operating temperature range) of the traditional fluorinated fluids, while being manufactured cost-effectively.

Generally, the present disclosure provides a new class of hydrofluorinated compounds useful as working fluids. The new compounds are unsaturated hydrofluorinated compounds comprising an amine and/or ether. The compounds of the present disclosure provide similar physical properties to existing fluorinated fluids, but generally exhibit shorter atmospheric lifetimes leading to lower global warming potentials. Typically, saturated perfluorocarbons have atmospheric lifetimes of greater than 2,000 years, saturated hydrofluorocarbons have atmospheric lifetimes of greater than 10 years and saturated hydrofluoroethers have atmospheric lifetimes of from 0.8 to 25 years. In one embodiment, the compounds of the present disclosure have atmospheric lifetimes of less than 1 year, 0.5 years, or even less than 0.1 years.

Surprisingly, in one embodiment, the compounds of the present disclosure can be readily prepared in high yield via low cost starting materials. The starting materials can be readily purchased or derived from electrochemical fluorination. Thus, the compounds described in the present disclosure represent a new class of useful and potentially low cost fluorinated fluids that offer potential advantages in a variety of applications including cleaning, solvent-based coating deposition, heat transfer, foam blowing, fire extinguishing, and battery electrolyte applications.

The unsaturated fluorinated compound of the present disclosure (herein referred to interchangeably as a compound of the present disclosure) are of the general formula (I)

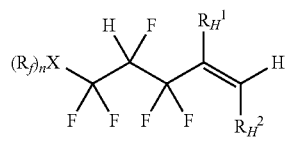

where
$R_H^1$ is and $R_H^2$ are independently selected from H or $CH_3$, wherein when $R_H^1$ is $CH_3$ than $R_H^2$ is H and when $R_H^2$ is $CH_3$ than $R_H^1$ is H; and
X is O or N, when
(a) X is O, then n is 1 and $R_f$ is a linear or branched perfluorinated alkyl group comprising 1-10 carbon atoms and optionally comprising at least one catenated O or N atom;
(b) X is N, then n is 2 and (i) each $R_f$ is independently selected from a linear or branched perfluorinated alkyl group comprising 1-8 carbon atoms and optionally comprising at least one catenated O or N atom, or (ii) the two $R_f$'s are bonded together to form a perfluorinated ring structure comprising no more than 10 carbon atoms, optionally comprising at least one catenated O or N atom, and wherein the ring of the ring structure consists of 5-7 atoms.

It is noted that when the compound comprises more than one catenated O or N atoms, the catenated O or N atoms form an ether or amine linkage, respectively. In other words, there are not two or more catenated O or N atoms located adjacent to one another.

In one embodiment, $R_H^1$ and $R_H^2$ are H.

In one embodiment, each $R_f$ is independently selected from a linear or branched perfluorinated alkyl group comprising 1, 2, 3, 4, 5, 6, 7, or even 8 carbon atoms. Optionally, $R_f$ comprises at least one catenated O or N atom (i.e., an ether or amine linkage), which is not next to X. Exemplary $R_f$ groups include: —$CF_3$, —$CF_2CF_3$, —$CF_2CF_2CF_3$, —$CF(CF_3)CF_3$, —$CF_2CF_2CF_2CF_3$, and —$CF_2CF_2OCF_3$.

In one embodiment, when X is nitrogen, the two $R_f$'s are bonded together to form a a 5, 6, or 7-membered ring. The $(R_f)_n X$— structure may comprise no more than 10 carbon atoms and may optionally comprise at least one catenated O or N atom. The at least one catenated O or N atom may be part of the ring or located on a substituent off the ring. Exemplary substituents off of the ring include perfluorinated alkyl groups, perfluorinated alkyl ether groups, and perfluorinated alkyl amine groups, which may comprise 1-6 carbon atoms.

In one embodiment, the two $R_f$'s are bonded together to form a 6-membered ring comprising a catenated O atom, forming for example a perfluorinated morpholine ring. In another embodiment, the two $R_f$'s are bonded together in a ring structure comprising an additional catenated nitrogen atom, wherein said additional nitrogen heteroatom is tertiary and is bonded to a perfluoroalkyl group having 1-3 carbon atoms. In one embodiment, the two $R_f$'s are bonded together to form a 6-membered ring comprising an additional catenated nitrogen atom, forming for example a perfluorinated piperazine ring, wherein said additional nitrogen heteroatom is tertiary and is bonded to a perfluoroalkyl group having 1-3 carbon atoms. In one embodiment, the two $R_f$'s are bonded together to form a perfluorinated pyrrolidine group.

In some embodiments, the compound of the present disclosure may have a degree of fluorination that is at least 70%, 75%, 80%, 85% or 90%. In other words, at least 70%, 75%, 80%, 85% or 90% of the C—H bonds in the molecule are replaced by C—F bonds.

Exemplary amine-containing hydrofluoroolefins of the present disclosure include:

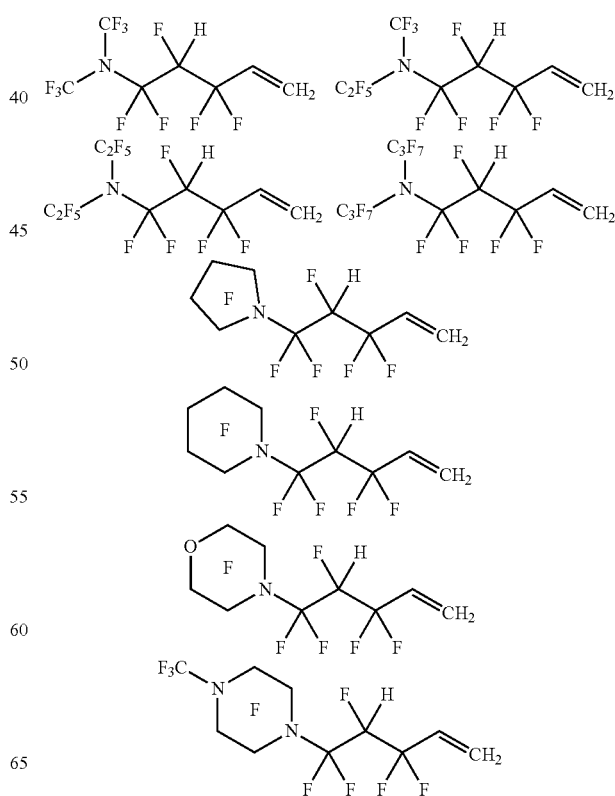

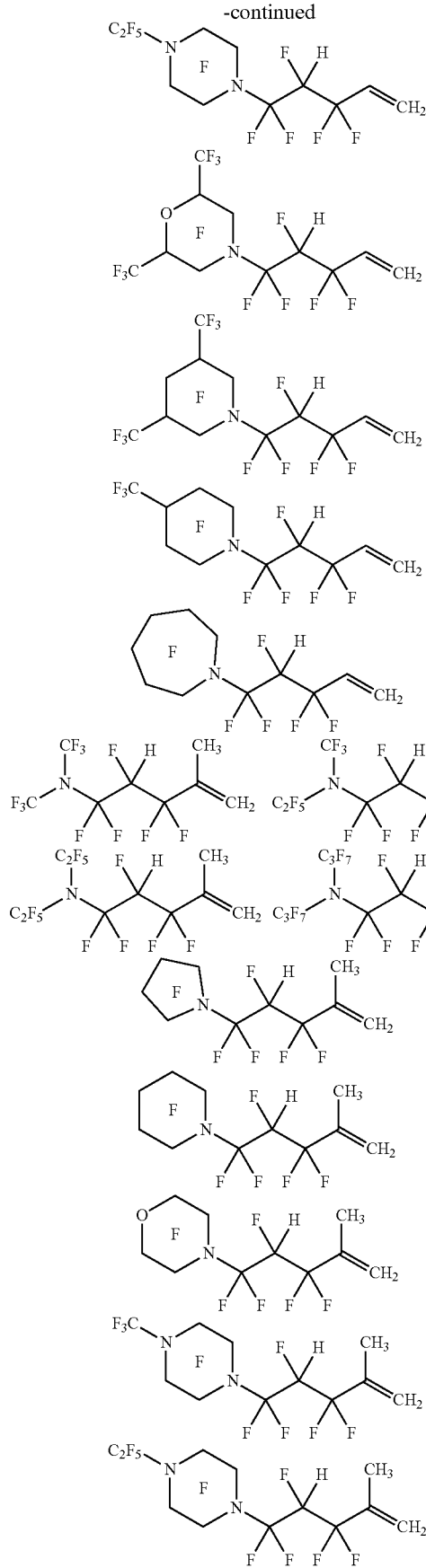
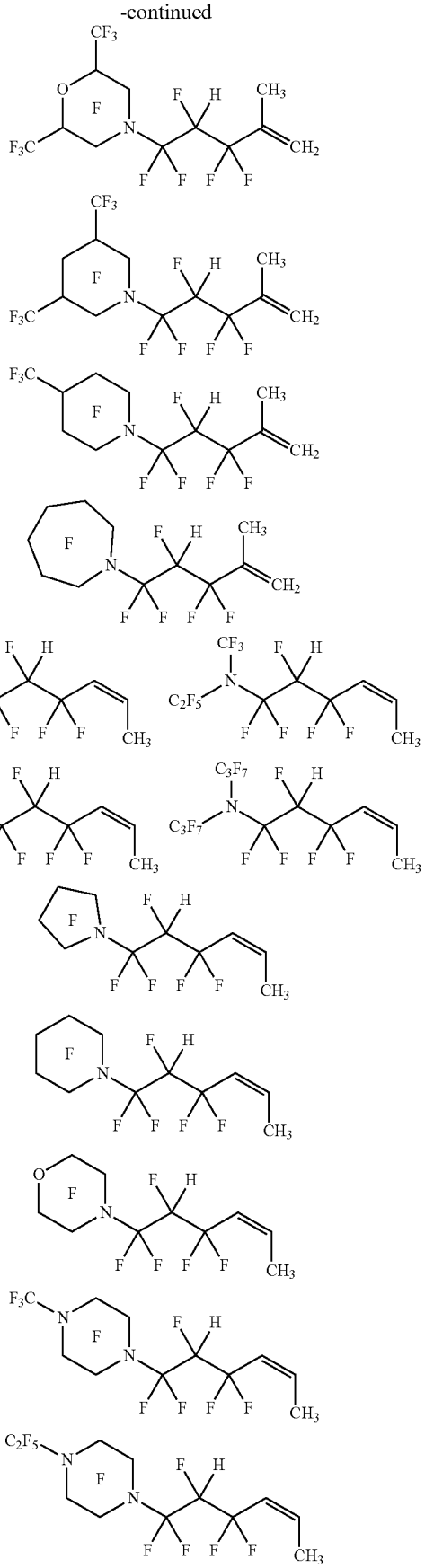

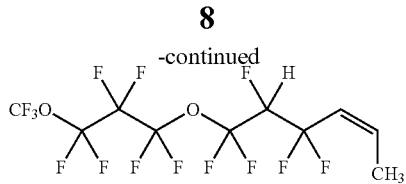

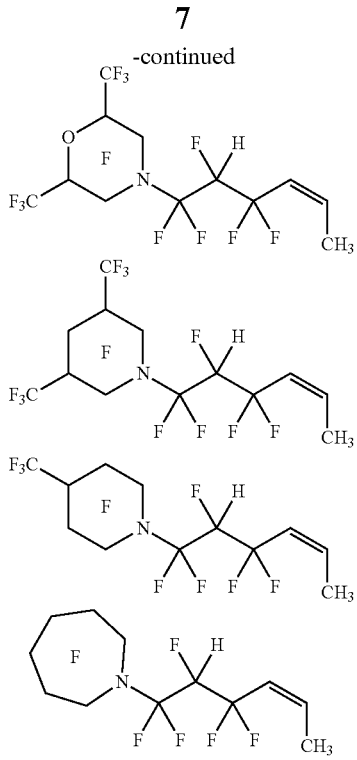

and combinations thereof.

Exemplary ether-containing hydrofluoroolefins of the present disclosure include:

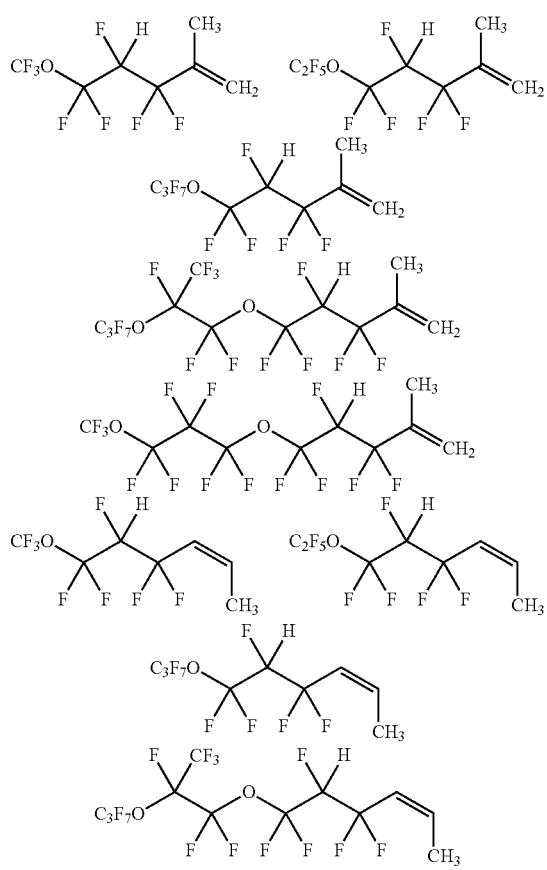

and combinations thereof.

For purposes of the present disclosure, it is to be appreciated that the unsaturated fluorinated compounds disclosed herein may include the E isomer, the Z isomer, or a mixture of the E and Z isomers, irrespective of what is depicted in any of the general formulas or chemical structures.

Non-flammability can be assessed by using standard methods such as ASTM D-3278-96 e-1, D56-05 "Standard Test Method for Flash Point of Liquids by Small Scale Closed-Cup Apparatus". In one embodiment, the compound of the present disclosure is non-flammable based on closed-cup flashpoint testing following ASTM D-327-96 e-1.

In one embodiment, the compound of the present disclosure may have a low environmental impact. In this regard, the compounds of the present disclosure may have a global warming potential (GWP) of less than 100 or even less than 10. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i [C(t)] dt}{\int_0^{ITH} a_{CO_2} [C_{CO_2}(t)] dt} = \frac{\int_0^{ITH} a_i C_{oi} e^{-t/\tau_i} dt}{\int_0^{ITH} a_{CO_2} [C_{CO_2}(t)] dt}$$

In this equation $a_1$ is the radiative forcing per unit mass increase of a compound in the atmosphere (the change in the flux of radiation through the atmosphere due to the IR absorbance of that compound), C is the atmospheric concentration of a compound, $\tau$ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In one embodiment, the compound of the present disclosure is expected to be non-toxic.

In one embodiment, the compound of the present disclosure is non-bioaccumulative in animal tissues. For example, some compounds of the present disclosure may provide low log $K_{ow}$ values, indicating a reduced tendency to bioaccumulate in animal tissues, where $K_{ow}$ is the octanol/water partition coefficient which is defined as the ratio of the given compound's concentration in a two-phase system comprising an octanol phase and an aqueous phase.

In one embodiment, the compound of the present disclosure has a boiling point of at least 60° C., 80° C., 100°, 150° C., or even 200° C.

In some embodiments, the compound of the present disclosure may be hydrophobic, relatively chemically unreactive, and thermally stable.

The compounds of the present disclosure can be accomplished by a variety of synthetic methods, which are described below.

In one embodiment, the compound of the present disclosure may be prepared by the free radical addition of a primary or secondary alcohol (III) to a perfluorinated allylic compound (II); followed by acylation to form a fluorinated ester. The fluorinated ester is then vapor phase dehydroacetoxylated (VPD) to form the compounds of the present disclosure (I). A general reaction is shown in Scheme 1:

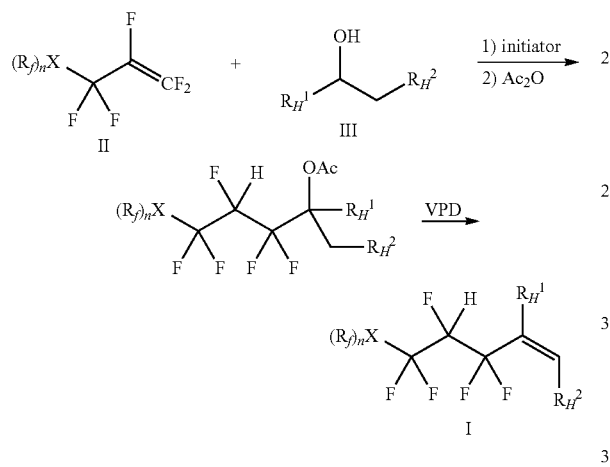

Starting alcohol (III) can be a primary alcohol or a secondary alcohol. If it is a primary alcohol, then at least one of $R_H^1$ or $R_H^2$ is H. The primary and secondary alcohols are not fluorinated (i.e., do not comprise any F atoms). Exemplary starting alcohols include: ethanol, 1-propanal, and 2-propanol.

The starting alcohol is reacted with a perfluorinated allylic compound (II), including a perfluorinated allyl ether, or a perfluorinated allyl amine.

In some embodiments, the perfluorinated allyl ether starting materials can be prepared from the allylation of perfluorinated metal alkoxide. Perfluorinated metal alkoxides are intermediates prepared by contacting a perfluorinated acid fluoride with a metal fluoride source in the presence of a solvent, such as diglyme. Such a synthesis is described in Krespan et al., J. Am. Chem. Soc., v. 103, pages 5598-5599 (1981).

Exemplary perfluorinated allyl ethers include:

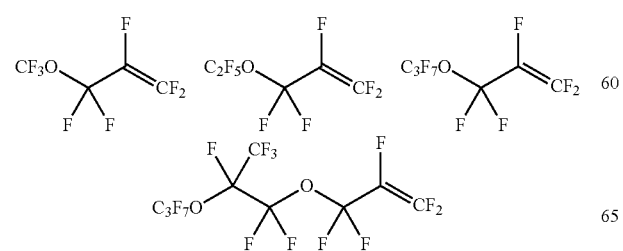

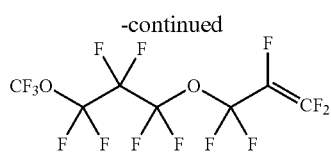

In some embodiments, the perfluorinated allyl amine starting materials can be prepared by electrochemical perfluorination of the appropriate nitrogen containing hydrocarbon carboxylate derivatives followed by decarboxylation of the perfluorinated nitrogen-containing carboxylates using procedures that are known in the art. Specifically, the perfluorinated acid fluorides, and allyl amines can be prepared by synthetic procedures known in the art. See for example, U.S. Pat. No. 4,985,556 (Abe et al.).

Exemplary perfluorinated allyl amines include:

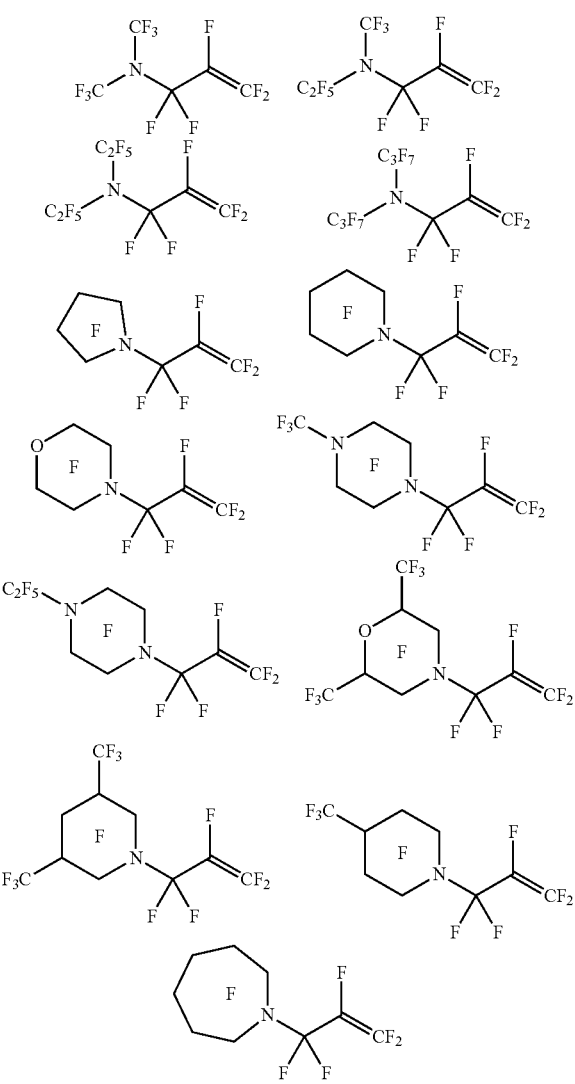

The starting alcohol and a perfluorinated allylic compound are reacted together such that the starting alcohol free radically adds to the perfluorinated allylic compound to from a second alcohol-containing compound. This second alcohol-containing compound is a secondary alcohol if a primary starting alcohol was used. This second alcohol-containing compound is a tertiary alcohol if a secondary starting alcohol was used.

The free radical addition of the starting alcohol to the perfluorinated allylic compound is promoted by suitable free radical initiators including peroxides, peroxyesters, or peroxycarbonates. Examples of such initiators include tert-amylperoxy-2-ethylhexanoate (TAPEH, available under the trade designation "LUPEROX 575" from Arkema, Crosby, Tex.), lauryl peroxide, tert-butyl peroxide, tert-amylperoxy-2-ethylhexyl carbonate, and mixtures thereof, with tert-amylperoxy-2-ethylhexanoate being the preferred initiator.

For the free radical addition reaction, typically the starting alcohol, perfluorinated allylic compound, and the initiator can be combined in a reactor (for example, a glass reactor or a metal pressure reactor) in any order, and the reaction can be run at a desired temperature with agitation. In one embodiment, the run temperature is from ambient to about 100° C. After reacting, the mixture can be cooled and the fluorous layer collected and distilled to isolate the second alcohol-containing compound.

The second alcohol-containing compound is then acylated to form a fluorinated ester. For the acylation step, the second alcohol-containing compound is combined with acetic anhydride in the presence of a heterogeneous catalyst. Such a catalyst includes acidic bentonite commercially available as Montmorillonite K-10. The mixture can be heated to facilitate the reaction. In one embodiment, the run temperature is from ambient to about 100° C. After reacting, the mixture can be cooled and the fluorous layer collected and washed to remove the starting materials and isolate the fluorinated ester.

The fluorinated ester then undergoes vapor phase dehydroacetoxylation to form the compound of the present disclosure. In one embodiment, the vapor phase dehydroacetoxylation is carried out by heating the fluorinated ester under the flow of an inert gas and in the presence of a packing material. Exemplary packing materials include helices, glass beads, glass wool, borosilicate beads, etc. Temperatures range from at least 450° C. to at most 550° C. Inert gases include for example nitrogen and argon. Such vapor phase dehydroacetoxylation is described in Bailey et al., J. Org. Chem., v. 21, pages 543-545 (1956); Froemsdorf et al., J. Am. Chem. Soc., v. 81, pages 643-647 (1959); and Bailey et al., J. Am. Chem. Soc., vol. 81, pages 647-651 (1959).

In another embodiment, the compound of the present disclosure may be prepared by the free radical addition of a primary or secondary alcohol (III) to a perfluorinated allylic compound (II) to form a second alcohol-containing compound, followed by dehydration to form the compounds of the present disclosure (I). A general reaction is shown in Scheme 2:

Scheme 2

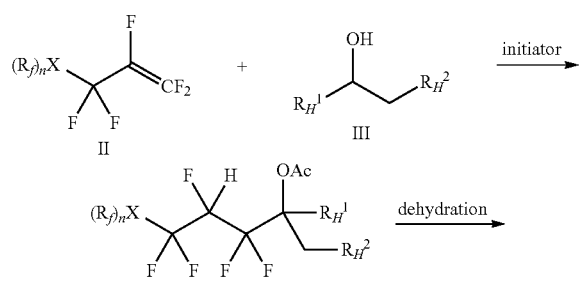

-continued

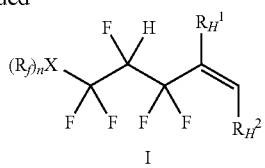

The dehydration may be carried out by heating the second alcohol-containing compound in the presence of a dehydrating agent. An exemplary dehydrating agent includes phosphorus pentoxide. Temperatures may range from at least 150° C. to at most 250° C.

In one embodiment, the resulting fluorinated compounds can be purified to isolate the desired nitrogen and/or oxygen-containing hydrofluoroolefin. Purification can be done by conventional means including distillation, absorption, extraction, chromatography and recrystallization. The purification can be done to isolate the compound of the present disclosure (in all of its stereoisomeric forms) from impurities, such as starting materials, byproducts, etc. The term "purified form" as used herein means the compound of the present disclosure is at least 90, 95, 98, or even 99 wt % pure.

The compounds of the present disclosure may be used as a working fluid in a variety of applications. The working fluids may include at least 25%, 50%, 70%, 80%, 90%, 95%, 99%, or even 100% by weight of the above-described formula (I) compounds based on the total weight of the working fluid. In addition to the compounds of the present disclosure, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, unsaturated hydrochlorocarbons, unsaturated hydrochlorofluorocarbons, unsaturated hydrofluorocarbons, non-hetero atom-containing hydrofluoroolefins, hydrochloroolefins, hydrochlorofluoroolefins, unsaturated hydrofluoroethers, or mixtures thereof, based on the total weight of the working fluid. Such additional components can be chosen to modify or enhance the properties of a composition for a particular use.

In one embodiment, the working fluid has no flash point (as measured, for example, following ASTM D-3278-96 e-1).

In one embodiment, the compound of the present disclosure is used in a cleaning compositions along with one or more co-solvents. In some embodiments, the present disclosure relates to a process for cleaning a substrate. The cleaning process can be carried out by contacting a contaminated substrate with a cleaning composition. The compound of the present disclosure can be utilized alone or in admixture with each other or with other commonly-used cleaning co-solvents. Representative examples of co-solvents that can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof. Such co-solvents can be chosen to modify or enhance the solvency properties of a cleaning composition for a particular use and can be utilized in ratios (of co-solvent to compounds according to formula (I)) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more compounds of the present disclosure and optionally one or more surfactants. Suitable surfactants include those surfactants that are sufficiently soluble in the compound of the present disclosure, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In one embodiment, the compound of the present disclosure may be used in an apparatus for heat transfer that includes a device and a mechanism for transferring heat to or from the device. The mechanism for transferring heat may include a heat transfer working fluid that includes a compound of formula (I) of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In another embodiment, the compound of the present disclosure is used as a fire extinguishing composition. The composition may include one or more compounds according to formula (I) and one or more co-extinguishing agents.

In illustrative embodiments, the co-extinguishing agent may include unsaturated hydrofluorocarbons, unsaturated hydrochlorofluorocarbons, unsaturated perfluorocarbons, unsaturated perfluoropolyethers, unsaturated hydrofluoroethers, unsaturated hydrofluoropolyethers, unsaturated chlorofluorocarbons, unsaturated bromofluorocarbons, unsaturated bromochlorofluorocarbons, unsaturated hydrobromocarbons, unsaturated iodofluorocarbons, unsaturated fluorinated ketones, perfluorocarbons, unsaturated hydrobromofluorocarbons, perfluorinated olefins, non-hetero atom-containing hydrofluoroolefins, fluorinated sulfones, fluorinated vinylethers, unsaturated fluoroethers, bromofluoroolefins, chlorofluoroolefins, iodofluoroolefins, fluorinated vinyl amines, fluorinated aminopropenes and mixtures thereof.

Such co-extinguishing agents can be chosen to enhance the extinguishing capabilities or modify the physical properties (e.g., modify the rate of introduction by serving as a propellant) of an extinguishing composition for a particular type (or size or location) of fire and can preferably be utilized in ratios (of co-extinguishing agent to the compound of formula (I)) such that the resulting composition does not form flammable mixtures in air.

In some embodiments, the compounds of formula (I) and the co-extinguishing agent may be present in the fire extinguishing composition in amounts sufficient to suppress or extinguish a fire. The compound of formula (I) and the co-extinguishing agent can be in a weight ratio of from about 9:1 to about 1:9.

In another embodiment, the compound of the present disclosure is used in an apparatus for converting thermal energy into mechanical energy in a Rankine cycle. The apparatus may include a working fluid that includes one or more compounds of formula (I). The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more compounds of formula (I) to form a vaporized working fluid. In some embodiments, the heat is transferred from the heat source to the working fluid in an evaporator or boiler. The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

In yet another embodiment, the compound of the present disclosure is used as nucleating agents in the production of polymeric foams and in particular in the production of polyurethane foams and phenolic foams. In this regard, in some embodiments, the present disclosure is directed to a foamable composition that includes one or more blowing agents, one or more foamable polymers or precursor compositions thereof, and one or more nucleating agents that include a compound of formula (I).

In some embodiments, a variety of blowing agents may be used in the provided foamable compositions including liquid or gaseous blowing agents that are vaporized in order to foam the polymer or gaseous blowing agents that are generated in situ in order to foam the polymer. Illustrative examples of blowing agents include unsaturated hydrochlorofluorocarbons, unsaturated hydrofluorocarbons, unsaturated hydrochlorocarbons, unsaturated iodofluorocarbons, unsaturated hydrocarbons, non-hetero atom-containing hydrofluoroolefins, and unsaturated hydrofluoroethers. The blowing agent for use in the provided foamable compositions can have a boiling point of from about −45° C. to about 100° C. at atmospheric pressure. Typically, at atmospheric pressure the blowing agent has a boiling point of at least about 15° C., more typically between about 20° C. and about 80° C. The blowing agent can have a boiling point of between about 30° C. and about 65° C. Further illustrative examples of blowing agents that can be used in the invention include aliphatic and cycloaliphatic hydrocarbons having about 5 to about 7 carbon atoms, such as n-pentane and cyclopentane, esters such as methyl formate, unsaturated hydrofluorocarbons such as $CF_3CF_2CHFCHFCF_3$, $CF_3CH_2CF_2H$, $CF_3CH_2CF_2CH_3$, $CF_3CF_2H$, $CH_3CF_2H$ (HFC-152a), $CF_3CH_2CH_2CF_3$ and $CHF_2CF_2CH_2F$, unsaturated hydrochlorofluorocarbons such as $CH_3CCl_2F$, $CF_3CHCl_2$, and $CF_2HCl$, unsaturated hydrocarbons such as 2-chloropropane, and unsaturated iodofluorocarbons such as $CF_3I$, and unsaturated hydrofluoroethers such as $C_4F_9OCH_3$ and non-hetero atom-containing hydrofluoroolefin such as $CF_3CF=CH_2$, $CF_3CH=CHF$, $CF_3CH=CHCl$ and $CF_3CH=CHCF_3$. In certain formulations $CO_2$ generated from the reaction of water with foam precursor such as an isocyanate can be used as a blowing agent.

In various embodiments, the provided foamable composition may also include one or more foamable polymers or a precursor composition thereof. Foamable polymers suitable for use in the provided foamable compositions include, for example, polyolefins, e.g., polystyrene, poly(vinyl chloride), and polyethylene. Foams can be prepared from styrene polymers using conventional extrusion methods. The blowing agent composition can be injected into a heat-plastified styrene polymer stream within an extruder and admixed therewith prior to extrusion to form foam. Representative examples of suitable styrene polymers include, for example, the solid homopolymers of styrene, α-methylstyrene, ring-alkylated styrenes, and ring-halogenated styrenes, as well as copolymers of these monomers with minor amounts of other readily copolymerizable olefinic monomers, e.g., methyl methacrylate, acrylonitrile, maleic anhydride, citraconic anhydride, itaconic anhydride, acrylic acid, N-vinylcarbazole, butadiene, and divinylbenzene. Suitable vinyl chloride polymers include, for example, vinyl chloride homopolymer and copolymers of vinyl chloride with other vinyl monomers. Ethylene homopolymers and copolymers of ethylene with, e.g., 2-butene, acrylic acid, propylene, or butadiene may also be useful. Mixtures of different types of polymers can be employed.

In various embodiments, the foamable compositions of the present disclosure may have a molar ratio of nucleating agent to blowing agent of no more than 1:50, 1:25, 1:9, or 1:7, 1:3, or 1:2.

Other conventional components of foam formulations can, optionally, be present in the foamable compositions of the present disclosure. For example, cross-linking or chain-extending agents, foam-stabilizing agents or surfactants, catalysts and fire-retardants can be utilized. Other possible components include fillers (e.g., carbon black), colorants, fungicides, bactericides, antioxidants, reinforcing agents, antistatic agents, and other additives or processing aids.

In some embodiments, polymeric foams can be prepared by vaporizing at least one liquid or gaseous blowing agent or generating at least one gaseous blowing agent in the presence of at least one foamable polymer or a precursor composition thereof and a nucleating agent as described above. In further embodiments, polymeric foams can be prepared using the provided foamable compositions by vaporizing (e.g., by utilizing the heat of precursor reaction) at least one blowing agent in the presence of a nucleating agent as described above, at least one organic polyisocyanate and at least one compound containing at least two reactive hydrogen atoms. In making a polyisocyanate-based foam, the polyisocyanate, reactive hydrogen-containing compound, and blowing agent composition can generally be combined, thoroughly mixed (using, e.g., any of the various known types of mixing head and spray apparatus), and permitted to expand and cure into a cellular polymer. It is often convenient, but not necessary, to preblend certain of the components of the foamable composition prior to reaction of the polyisocyanate and the reactive hydrogen-containing compound. For example, it is often useful to first blend the reactive hydrogen-containing compound, blowing agent composition, and any other components (e.g., surfactant) except the polyisocyanate, and to then combine the resulting mixture with the polyisocyanate. Alternatively, all components of the foamable composition can be introduced separately. It is also possible to pre-react all or a portion of the reactive hydrogen-containing compound with the polyisocyanate to form a prepolymer.

In still another embodiment, the compound of the present disclosure is used in a dielectric fluids, which can be used in electrical devices (e.g., capacitors, switchgear, transformers, or electric cables or buses). For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more compounds of formula (I) and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application comprising the compounds of formula (I) are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In another embodiment, the present disclosure relates to coating compositions comprising (a) a solvent composition that includes one or more compounds of the present disclosure, and (b) one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include unsaturated perfluoropolyether, unsaturated hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, unsaturated perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the compounds of Formula (I) function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more of the compounds of formula (I); and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the compound(s) of formula (I), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure further relates to electrolyte compositions that include one or more compounds of the present disclosure. The electrolyte compositions may comprise (a) a solvent composition including one or more of the compounds according to formula (I); and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. Li/Li$^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, a bis(perfluoroalkanesulfonyl)imide anion); that are at least partially soluble in a selected compound of formula (I) (or in a blend thereof with one or more other compounds of formula (I) or one or more conventional electrolyte solvents); and that at least partially dissociate to form a conductive electrolyte composition. The salts may be stable over a range of operating voltages, are non-corrosive, and are thermally and hydrolytically stable. Suitable cations include alkali metal, alkaline earth metal, Group IIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $PF_6^-$, $AsF_6^-$, and $SbF_6^-$; $ClO_4^-$; $HSO_4^-$; $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, (perfluoroalkanesulfonyl)imides, bis(perfluoroalkanesulfonyl) methides, and tris(perfluoroalkanesulfonyl)methides; and the like. Preferred anions for battery use include fluorine-containing inorganic anions (for example, $(FSO_2)_2N^-$, $PF_6^-$, and $AsF_6^-$) and fluorine-containing organic anions (for example, perfluoroalkanesulfonates, bis(perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated. The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris(perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(fluorosulfonyl)imide (Li-FSI), and mixtures of two or more thereof.

The electrolyte compositions of the present disclosure can be prepared by combining at least one electrolyte salt and a solvent composition including at least one compound of formula (I), such that the salt is at least partially dissolved in the solvent composition at the desired operating temperature. The compounds of the present disclosure (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the compound(s) of formula (I) (for example, such that the compound(s) of formula (I) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, 7-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1, 3-dioxolane, alkyl-substituted 1, 3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cell may include a positive electrode, a negative electrode, a separator, and the above-described electrolyte composition.

A variety of negative and positive electrodes may be employed in the electrochemical cells. Representative negative electrodes include graphitic carbons e.g., those having a spacing between (002) crystallographic planes, $d_{002}$, of 3.45 Å$>d_{002}>$3.354 Å and existing in forms such as powders, flakes, fibers or spheres (e.g., mesocarbon microbeads); $Li_{4/3}Ti_{5/3}O_4$ the lithium alloy compositions described in U.S. Pat. No. 6,203,944 (Turner et al.) and U.S. Pat. No. 6,255,017 (Turner); and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e.g., carbon black for negative electrodes and carbon black, flake graphite and the like for positive electrodes.

The electrochemical devices of the invention can be used in various electronic articles such as computers, power tools, automobiles, telecommunication devices, and the like.

Exemplary embodiments include, but are not limited to, the following embodiments:

Embodiment 1. An unsaturated fluorinated compound of formula (I)

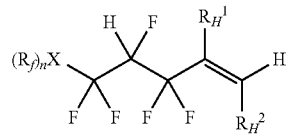

where
RH1 is and RH2 are independently selected from H or CH3, wherein when RH1 is CH3 than RH2 is H and when RH2 is CH3 than RH1 is H;
X is O or N and when
X is O, then n is 1 and Rf is a linear or branched perfluorinated alkyl group comprising 1-10 carbon atoms and optionally comprising at least one catenated O or N atom;
X is N, then n is 2 and (i) each Rf is independently selected from a linear or branched perfluorinated alkyl group comprising 1-8 carbon atoms and optionally comprising at least one catenated O or N atom, or (ii) the two Rf's are bonded together to form a perfluorinated ring structure comprising no more than 10 carbon atoms, optionally comprising at least one catenated O or N atom, and wherein the ring of the ring structure consists of 5-7 atoms.

Embodiment 2. The unsaturated fluorinated compound of embodiment 1, wherein RH1 and RH2 are H.

Embodiment 3. The unsaturated fluorinated compound of any one of the previous embodiments, wherein when X is O, Rf comprises 1 to 3 carbon atoms.

Embodiment 4. The unsaturated fluorinated compound of any one of embodiments 1-2, wherein when X is N, the two Rf's are bonded together to form a ring structure optionally comprising at least one catenated O or N atom and no more than 7 carbon atoms.

Embodiment 5. The unsaturated fluorinated compound of embodiment 1 or 2, wherein X is N and the two Rf's is bonded together to form a 6-membered perfluorinated ring comprising a catenated O atom.

Embodiment 6. The unsaturated fluorinated compound of embodiment 5, wherein the two Rf's form a morpholine group.

Embodiment 7. The unsaturated fluorinated compound of embodiment 1 or 2, wherein the two Rf's are bonded together to form a 6-membered perfluorinated ring comprising an additional catenated N atom.

Embodiment 8. The unsaturated fluorinated compound of embodiment 7, wherein the two Rf's form an N-perfluoroalkyl piperazine group.

Embodiment 9. The unsaturated fluorinated compound of embodiment 8, wherein the perfluoroalkyl is linear or branched and comprises 1-3 carbon atoms.

Embodiment 10. The unsaturated fluorinated compound of embodiment 1 or 2, wherein the two Rf's form a pyrrolidine group.

Embodiment 11. The unsaturated fluorinated compound of embodiment 1, wherein the unsaturated fluorinated compound is selected from:

Embodiment 12. The unsaturated fluorinated compound of any one of the previous embodiments, wherein the unsaturated fluorinated compound has a degree of fluorination of at least 70%.

Embodiment 13. The unsaturated fluorinated compound of any one of the previous embodiments, wherein the unsaturated fluorinated compound is nonflammable based on closed-cup flashpoint testing following ASTM D-327-96 e-1.

Embodiment 14. The unsaturated fluorinated compound of any one of the previous embodiments, wherein the unsaturated fluorinated compound has a global warming potential of less than 100.

Embodiment 15. A composition comprising a purified form of the unsaturated fluorinated compound according to any one of the previous embodiments.

Embodiment 16. A working fluid comprising the unsaturated fluorinated compound according to any one of embodiments 1-12, wherein the unsaturated fluorinated compound is present in the working fluid in an amount of at least 5% by weight based on the total weight of the working fluid.

Embodiment 17. The working fluid of embodiment 16, wherein the working fluid further comprises a co-solvent.

Embodiment 18. Use of the unsaturated fluorinated compound of any one embodiments 1-14, wherein the unsaturated fluorinated compound is in a cleaning composition.

Embodiment 19. Use of the unsaturated fluorinated compound of any one embodiments 1-14, wherein the unsaturated fluorinated compound is an electrolyte solvent or additive.

Embodiment 20. Use of the unsaturated fluorinated compound of any one embodiments 1-14, wherein the unsaturated fluorinated compound is a heat transfer fluid.

Embodiment 21. Use of the unsaturated fluorinated compound of any one embodiments 1-14, wherein the unsaturated fluorinated compound is a vapor phase soldering fluid.

Embodiment 22. An apparatus for heat transfer comprising: a device; and a mechanism for transferring heat to or from the device, the mechanism comprising a heat transfer fluid that comprises the unsaturated fluorinated compound according to any one of embodiments 1-14.

Embodiment 23. An apparatus for heat transfer according to embodiment 22, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

Embodiment 24. An apparatus according to any one of embodiments 22-23, wherein the mechanism for transferring heat is a component in a system for maintaining a temperature or temperature range of an electronic device.

Embodiment 25. A method of making an unsaturated fluorinated compound, the method comprising:
(i) reacting a perfluorinated allylic compound with a first alcohol in the presence of a free radical initiator to form a second alcohol, wherein the perfluorinated allylic compound comprises a perfluorinated allylic ether or a perfluorinated allylic amine, the first alcohol is a primary alcohol or a secondary alcohol, and the second alcohol is a secondary or tertiary fluorinated alcohol;
(ii) acylating the second alcohol to form a fluorinated ester; and
(iii) vapor phase dehydroacetoxylating the fluorinated ester to form the unsaturated fluorinated compound.

Embodiment 26. The method of embodiment 25, wherein the acylating step uses a heterogeneous catalyst.

Embodiment 27. The method of embodiment 26, wherein the catalyst selected from and acidic bentonite.

Embodiment 28. The method of any one of embodiments 25-27, wherein the acylating step comprises acetic anhydride.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used in the following examples: mL=milliliters, L=liters, g=grams mmol=millimoles, min=minutes, h=hours, Pa=pascals, kPa=kilopascals, in=inches, cm=centimeters, mm=millimeters, GC=gas chromatography, and GC-MS=gas chromatography-mass spectrometry. Abbreviations for materials used in this section, as well as descriptions of the materials, are provided in Table 1.

TABLE 1

Materials List

| Material | Details |
| --- | --- |
| TAPEH | tert-Amylperoxy-2-ethylhexanoate, available under the trade designation "LUPEROX 575" from Arkema, Crosby, TX, USA. |
| Ethanol | 200 proof, available from Sigma-Aldrich Chemical Company |
| Acetic anhydride | Available from EMD Chemicals, Philadelphia, PA, USA |
| Montmorillonite K-10 | Available from Alfa Aesar, Ward Hill, MA, USA |
| Molecular sieves | 4 angstrom, available from Sigma-Aldrich Chemical Company |
| NaHCO$_3$ | Sodium bicarbonate, available from Sigma-Aldrich Chemical Company |
| MTBE | Methyl tert-butyl ether, available from Sigma-Aldrich Chemical Company |
| THF | Tetrahydrofuran, available from Sigma-Aldrich Chemical Company |
| Celite | available from Sigma-Aldrich Chemical Company |
| Water | Deionized water |
| 2,2,3,3,5,5,6,6-octafluoro-4-(perfluoroallyl)morpholine | May be synthesized by the procedure described in Example 22 in U.S. Pat. No. 4,985,556 to Abe et al. |
| 2,2,3,3,4,4,5,5-octafluoro-1-(perfluoroallyl)pyrrolidine | May be synthesized by the procedure described in Example 21 in U.S. Pat. No. 4,985,556 to Abe et al. |

TABLE 1-continued

Materials List

| Material | Details |
| --- | --- |
| 1,1,2,3,3-pentafluoro-N,N-bis(perfluoropropyl)prop-2-en-1-amine | May be synthesized by the methods described in U.S. Pat. No. 4,985,556 to Abe et al. |
| 1,1,2,3,3-pentafluoro-3-(perfluoropropoxy)prop-1-ene | May be synthesized by the methods described in Krespan et al. *J. Am. Chem. Soc.*, 1981, 5598-5599; Wlassics et al. Molecules, 2011, 6512-6540. |

Example 1 (EX-1) Preparation of 2,2,3,3,5,5,6,6-octafluoro-4-(1,1,2,3,3-pentafluoropent-4-en-1-yl)morpholine A 600 mL Parr reaction vessel was charged with ethanol (39.6 g, 860 mmol), TAPEH (1.8 g, 7.8 mmol), and 2,2,3,3,5,5,6,6-octafluoro-4-(perfluoroallyl)morpholine (49.1 g, 136 mmol). The resultant mixture was stirred overnight at 75° C. The reaction mixture was then heated to 90° C. followed by a 0.5 h stir to consume any unreacted initiator (TAPEH). After cooling to room temperature, water (100 mL) was added and the resultant mixture was transferred to a separatory funnel. The bottom, fluorous layer was collected and short-path distillation (57.9° C., 1.5 Torr (200 Pa)) afforded 3,3,4,5,5-pentafluoro-5-(perfluoromorpholino)pentan-2-ol (50.6 g, 91% yield based on 49.1 g 2,2,3,3,5,5,6,6-octafluoro-4-(perfluoroallyl)morpholine) as a colorless liquid. The distillate was stored over 4 angstrom molecular sieves and was used in the next step.

To a 250 mL two-neck, round-bottom flask equipped with a magnetic stir bar, water-cooled condenser, and addition funnel were added montmorillonite K-10 (1.04 g) and acetic anhydride (18.6 g, 182 mmol). The resultant mixture was heated to 70° C. To the stirring mixture was added 3,3,4,5,5-pentafluoro-5-(perfluoromorpholino)pentan-2-ol (24.9 g, 61.2 mmol) dropwise. The reaction mixture was allowed to stir overnight at the same temperature and was then cooled to room temperature and filtered over a pad of celite. After filtration, the pad was washed with MTBE (20 mL) and the filtrate was slowly neutralized by the slow addition of a saturated solution of NaHCO$_3$ (150 mL) with stirring. The mixture was transferred to a separatory funnel and the fluorous phase was isolated and then washed once more with a saturated solution of NaHCO$_3$ (100 mL). 3,3,4,5,5-Pentafluoro-5-(perfluoromorpholino)pentan-2-yl acetate (21.5 g, 78% yield based on 24.9 g of 3,3,4,5,5-pentafluoro-5-(perfluoromorpholino)pentan-2-ol) was used in the next step without further purification.

A 0.5 in (3.8 cm) diameter stainless steel tube was packed with 2 mm diameter borosilicate beads and fitted with a thermocouple, cold water condenser, preheater, and nitrogen line. The reaction tube was heated to an internal temperature of 520° C. with a nitrogen flow of 10 mL/min. The preheater was set to 200° C. The nitrogen flow was reduced to 3 mL/min and 3,3,4,5,5-Pentafluoro-5-(perfluoromorpholino)pentan-2-yl acetate (21.5 g, 47.9 mmol) was fed to the tube at a rate of 0.2 mL/min via a syringe pump. The mixture exiting the reaction tube was fed into a round-bottom flask containing a saturated solution of NaHCO$_3$ (50 mL) to neutralize acetic acid by-product. The fluorous phase was split from the aqueous phase. GC analysis indicated approximately 43% conversion of the acetate starting material to desired hydrofluoroolefin 2,2,3,3,5,5,6,6-octafluoro-4-(1,1,2,3,3-pentafluoropent-4-en-1-yl)morpholine) (6.72 g, 41% yield based on 21.5 g 3,3,4,5,5-Pentafluoro-5-(perfluoromorpholino)pentan-2-yl acetate). GC-MS analysis confirmed formation of the desired product.

Example 2 (EX-2) Preparation of 2,2,3,3,4,4,5,5-octafluoro-1-(1,1,2,3,3-pentafluoropent-4-en-1-yl)pyrrolidine A 300 mL Parr reaction vessel was charged with ethanol (32.7 g, 710 mmol), TAPEH (2.3 g, 10 mmol), and 2,2,3,3,4,4,5,5-octafluoro-1-(perfluoroallyl)pyrrolidine (50.1 g, 145 mmol). The resultant mixture was stirred overnight at 75° C. The reaction mixture was then heated to 90° C. followed by a 0.5 h stir to consume any unreacted initiator (TAPEH). After cooling to room temperature, water (100 mL) was added and the resultant mixture was transferred to a separatory funnel. The bottom, fluorous layer was collected and short-path distillation (176° C., 725 Torr (96.7 kPa)) afforded 3,3,4,5,5-pentafluoro-5-(perfluoropyrrolidin-1-yl)pentan-2-ol (47.3 g, 83% yield based on 50.1 g 2,2,3,3,4,4,5,5-octafluoro-1-(perfluoroallyl)pyrrolidine) as a colorless liquid. The distillate was stored over 4 angstrom molecular sieves and was used in the next step.

To a 250 mL two-neck, round-bottom flask equipped with a magnetic stir bar, water-cooled condenser, and addition funnel were added montmorillonite K-10 (0.94 g) and acetic anhydride (19.4 g, 190 mmol). The resultant mixture was heated to 70° C. To the stirring mixture was added 3,3,4,5,5-pentafluoro-5-(perfluoropyrrolidin-1-yl)pentan-2-ol (24.9 g, 63.7 mmol) dropwise. The reaction mixture was allowed to stir overnight at the same temperature and was then cooled to room temperature and filtered over a pad of celite. After filtration, the pad was washed with THF (30 mL) and the filtrate was slowly neutralized by the slow addition of a saturated solution of NaHCO$_3$ (150 mL) with stirring. The mixture was transferred to a separatory funnel and the fluorous phase was isolated and then washed once more with a saturated solution of NaHCO$_3$ (100 mL). 3,3,4,5,5-pentafluoro-5-(perfluoropyrrolidin-1-yl)pentan-2-yl acetate (16.5 g, 60% yield based on 24.9 g 3,3,4,5,5-pentafluoro-5-(perfluoropyrrolidin-1-yl)pentan-2-ol) was used in the next step without further purification.

A 0.5 in (3.8 cm) diameter stainless steel tube was packed with 2 mm borosilicate beads and fitted with a thermocouple, cold water condenser, preheater, and nitrogen line. The reaction tube was heated to an internal temperature of 520° C. with a nitrogen flow of 10 mL/min. The preheater was set to 200° C. The nitrogen flow was reduced to 3 mL/min and 3,3,4,5,5-pentafluoro-5-(perfluoropyrrolidin-1-yl)pentan-2-yl acetate (10.0 g, 23.1 mmol) was fed to the tube at a rate of 0.2 mL/min via a syringe pump. The mixture exiting the reaction tube was fed into a round-bottom flask containing a saturated solution of NaHCO$_3$ (50 mL) to neutralize acetic acid by-product. The fluorous phase was split from the aqueous phase. GC analysis indicated approximately 51% conversion of the acetate starting material to desired hydrofluoroolefin 2,2,3,3,4,4,5,5-octafluoro-1-(1,1,2,3,3-pentafluoropent-4-en-1-yl)pyrrolidine (4.0 g, 47% yield based on 10.0 g 3,3,4,5,5-pentafluoro-5-(perfluoropyrrolidin-1-yl)pentan-2-yl acetate). GC-MS analysis confirmed formation of the desired product.

Example 3 (EX-3) Preparation of 1,1,2,3,3-pentafluoro-N,N-bis(perfluoropropyl)pent-4-en-1-amine A 300 mL Parr reaction vessel was charged with ethanol (31.7 g, 688 mmol), TAPEH (2.1 g, 9.1 mmol), and 1,1,2, 3,3-pentafluoro-N,N-bis(perfluoropropyl)prop-2-en-1-amine (47.8 g, 99 mmol). The resultant mixture was stirred overnight at 75° C. The reaction mixture was then heated to 90° C. followed by a 0.5 h stir to consume any unreacted initiator (TAPEH). After cooling to room temperature, water (100 mL) was added and the resultant mixture was transferred to a separatory funnel. The bottom, fluorous layer was collected and short-path distillation (51.5° C., 0.2 Torr (26.7 kPa)) afforded 5-(bis(perfluoropropyl)amino)-3,3,4,5,5-pentafluoropentan-2-ol (45.4 g, 90% yield based on 47.8 g 1,1,2,3,3-pentafluoro-N,N-bis(perfluoropropyl)prop-2-en-1-amine) as a colorless liquid. The distillate was stored over 4 angstrom molecular sieves and was used in the next step.

To a 250 mL two-neck, round-bottom flask equipped with a magnetic stir bar, water-cooled condenser, and addition funnel were added montmorillonite K-10 (0.94 g) and acetic anhydride (15.8 g, 155 mmol). The resultant mixture was heated to 70° C. To the stirring mixture was added 5-(bis(perfluoropropyl)amino)-3,3,4,5,5-pentafluoropentan-2-ol (24.9 g, 47.1 mmol) dropwise. The reaction mixture was allowed to stir overnight at the same temperature and was then cooled to room temperature and filtered over a pad of celite. After filtration, the pad was washed with THF (30 mL) and the filtrate was slowly neutralized by the slow addition of a saturated solution of NaHCO$_3$ (150 mL) with stirring. The mixture was transferred to a separatory funnel and the fluorous phase was isolated and then washed once more with a saturated solution of NaHCO$_3$ (100 mL). 5-(bis(perfluoropropyl)amino)-3,3,4,5,5-pentafluoropentan-2-yl acetate (22.3 g, 83% yield based on 24.9 g 5-(bis(perfluoropropyl)amino)-3,3,4,5,5-pentafluoropentan-2-ol) was used in the next step without further purification.

A 0.5 in (3.8 cm) diameter stainless steel tube was packed with 2 mm borosilicate beads and fitted with a thermocouple, cold water condenser, preheater, and nitrogen line. The reaction tube was heated to an internal temperature of 520° C. with a nitrogen flow of 10 mL/min. The preheater was set to 200° C. The nitrogen flow was reduced to 3 mL/min and 5-(bis(perfluoropropyl)amino)-3,3,4,5,5-pentafluoropentan-2-yl acetate (20 g, 35.0 mmol) was fed to the tube at a rate of 0.2 mL/min via a syringe pump. The mixture exiting the reaction tube was fed into a round-bottom flask containing a saturated solution of NaHCO$_3$ (50 mL) to neutralize acetic acid by-product. The fluorous phase was split from the aqueous phase. GC analysis indicated approximately 51% conversion of the acetate starting material to desired hydrofluoroolefin 1,1,2,3,3-pentafluoro-N,N-bis(perfluoropropyl)pent-4-en-1-amine (7.2 g, 40% yield based on 20 g 5-(bis(perfluoropropyl)amino)-3,3,4,5,5-pentafluoropentan-2-yl acetate). GC-MS analysis confirmed formation of the desired product.

Example 4 (EX-4) Preparation of 3,3,4,5,5-pentafluoro-5-(perfluoropropoxy)pent-1-ene A 300 mL Parr reaction vessel was charged with ethanol (32.0 g, 696 mmol), TAPEH (2.2 g, 9.6 mmol), and 1,1,2,3,3-pentafluoro-3-(perfluoropropoxy)prop-1-ene (23.8 g, 75.3 mmol). The resultant mixture was stirred overnight at 75° C. The reaction mixture was then heated to 90° C. followed by a 0.5 h stir to consume any unreacted initiator (TAPEH). After cooling to room temperature, water (100 mL) was added and the resultant mixture was transferred to a separatory funnel. The bottom, fluorous layer was collected and short-path distillation afforded 3,3,4,5,5-pentafluoro-5-(perfluoropropoxy)pentan-2-ol (22.3 g, 86% yield based on 23.8 g 1,1,2,3,3-pentafluoro-3-(perfluoropropoxy)prop-1-ene) as a colorless liquid. The distillate was stored over 4 angstrom molecular sieves and was used in the next step.

To a 250 mL two-neck, round-bottom flask equipped with a magnetic stir bar, water-cooled condenser, and addition funnel were added montmorillonite K-10 (0.94 g) and acetic anhydride (17 g, 167 mmol). The resultant mixture was heated to 70° C. To the stirring mixture was added 3,3,4,5,5-pentafluoro-5-(perfluoropropoxy)pentan-2-ol (14.9 g, 41.1 mmol) dropwise. The reaction mixture was allowed to stir overnight at the same temperature and was then cooled to room temperature and filtered over a pad of celite. After filtration, the pad was washed with THF (30 mL) and the filtrate was slowly neutralized by the slow addition of a saturated solution of NaHCO$_3$ (150 mL) with stirring. The mixture was transferred to a separatory funnel and the fluorous phase was isolated and then washed once more with a saturated solution of NaHCO$_3$ (100 mL). 3,3,4,5,5-pentafluoro-5-(perfluoropropoxy)pentan-2-yl acetate (13.7 g, 82% yield based on 14.9 g 3,3,4,5,5-pentafluoro-5-(perfluoropropoxy)pentan-2-ol) was used in the next step without further purification.

A 0.5 in (3.8 cm) diameter stainless steel tube was packed with 2 mm borosilicate beads and fitted with a thermocouple, cold water condenser, preheater, and nitrogen line. The reaction tube was heated to an internal temperature of 520° C. with a nitrogen flow of 10 mL/min. The preheater was set to 200° C. The nitrogen flow was reduced to 3 mL/min and 3,3,4,5,5-pentafluoro-5-(perfluoropropoxy)pentan-2-yl acetate (11.3 g, 28.0 mmol) was fed to the tube at a rate of 0.2 mL/min via a syringe pump. The mixture exiting the reaction tube was fed into a round-bottom flask containing a saturated solution of NaHCO$_3$ (50 mL) to neutralize acetic acid by-product. The fluorous phase was split from the aqueous phase. GC analysis indicated approximately 48% conversion of the starting material to desired hydrofluoroolefin 3,3,4,5,5-pentafluoro-5-(perfluoropropoxy)pent-1-ene (3.03 g, 32% yield based on 11.3 g 3,3,4,5,5-pentafluoro-5-(perfluoropropoxy)pentan-2-yl acetate). GC-MS analysis confirmed formation of the desired product.

Foreseeable modifications and alterations of this invention will be apparent to those skilled in the art without departing from the scope and spirit of this invention. This invention should not be restricted to the embodiments that are set forth in this application for illustrative purposes.

What is claimed is:
1. An unsaturated fluorinated compound of formula (I)

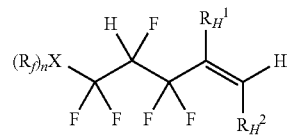

where
$R_H^1$ is and $R_H^2$ are independently selected from H or CH$_3$, wherein when $R_H^1$ is CH$_3$ then $R_H^2$ is H and when $R_H^2$ is CH$_3$ then $R_H^1$ is H;
X is O or N and when
X is O, then n is 1 and $R_f$ is a linear or branched perfluorinated alkyl group comprising 1-10 carbon atoms and optionally comprising at least one catenated O or N atom;

X is N, then n is 2 and (i) each $R_f$ is independently selected from a linear or branched perfluorinated alkyl group comprising 1-8 carbon atoms and optionally comprising at least one catenated O or N atom, or (ii) the two $R_f$'s are bonded together to form a perfluorinated ring structure comprising no more than 10 carbon atoms, optionally comprising at least one catenated O or N atom, and wherein the ring of the ring structure consists of 5-7 atoms.

2. The unsaturated fluorinated compound of claim 1, wherein $R_H^1$ and $R_H^2$ are H.

3. The unsaturated fluorinated compound of claim 1, wherein when X is O, Rf comprises 1 to 3 carbon atoms.

4. The unsaturated fluorinated compound of claim 1, wherein when X is N, the two $R_f$'s are bonded together to form a ring structure optionally comprising at least one catenated O or N atom and no more than 7 carbon atoms.

5. The unsaturated fluorinated compound of claim 1, wherein X is N and the two $R_f$'s is bonded together to form a 6-membered perfluorinated ring comprising a catenated O atom.

6. The unsaturated fluorinated compound of claim 5, wherein the two $R_f$'s form a morpholine group.

7. The unsaturated fluorinated compound of claim 1, wherein the two Rf's are bonded together to form a 6-membered perfluorinated ring comprising an additional catenated N atom.

8. The unsaturated fluorinated compound of claim 7, wherein the two Rf's form an N-perfluoroalkyl piperazine group.

9. The unsaturated fluorinated compound of claim 8, wherein the perfluoroalkyl is linear or branched and comprises 1-3 carbon atoms.

10. The unsaturated fluorinated compound of claim 1, wherein the two Rf's form a pyrrolidine group.

11. The unsaturated fluorinated compound of claim 1, wherein the unsaturated fluorinated compound is selected from:

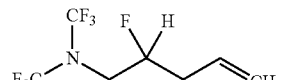
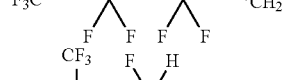
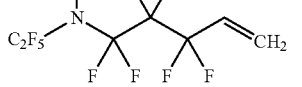
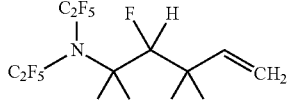
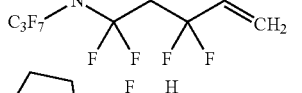

-continued

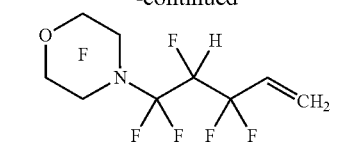
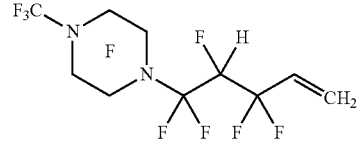
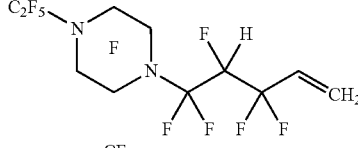
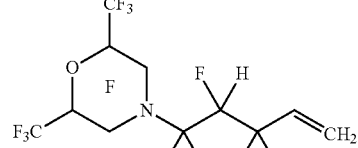
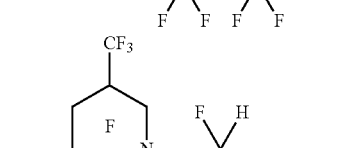
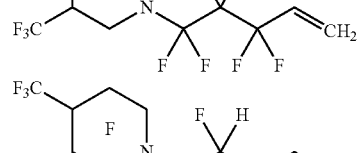
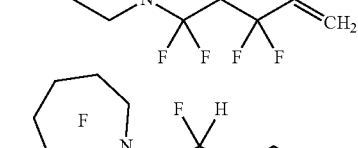
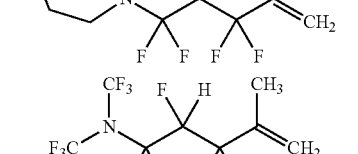
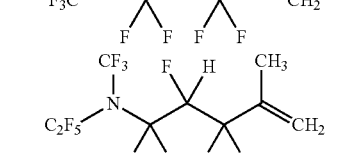
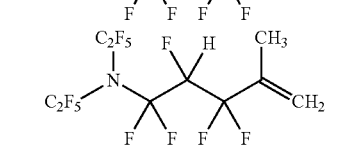
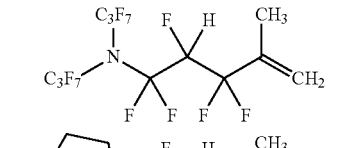
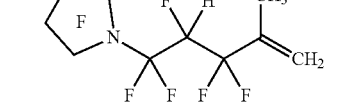

-continued
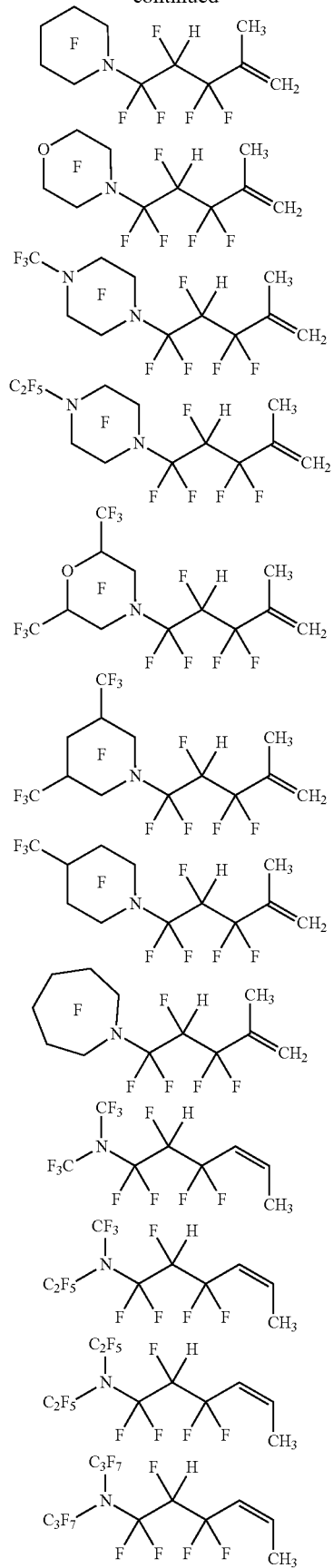
-continued
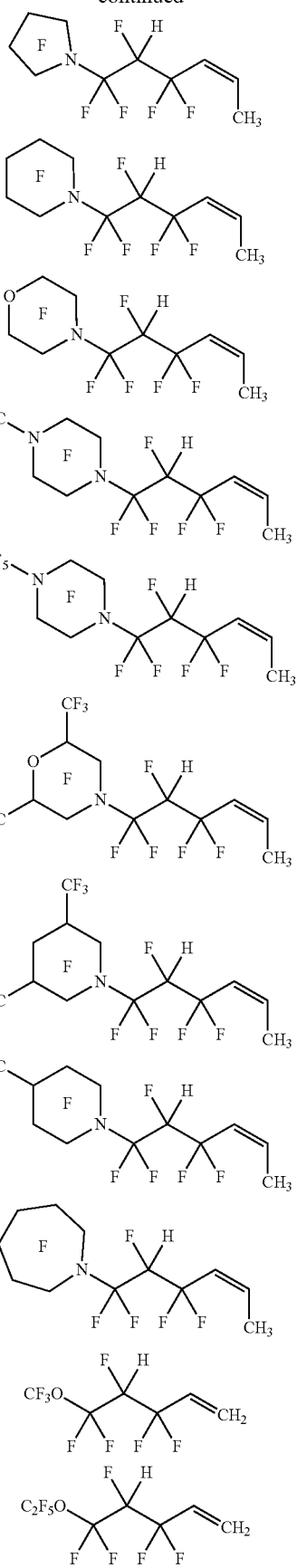

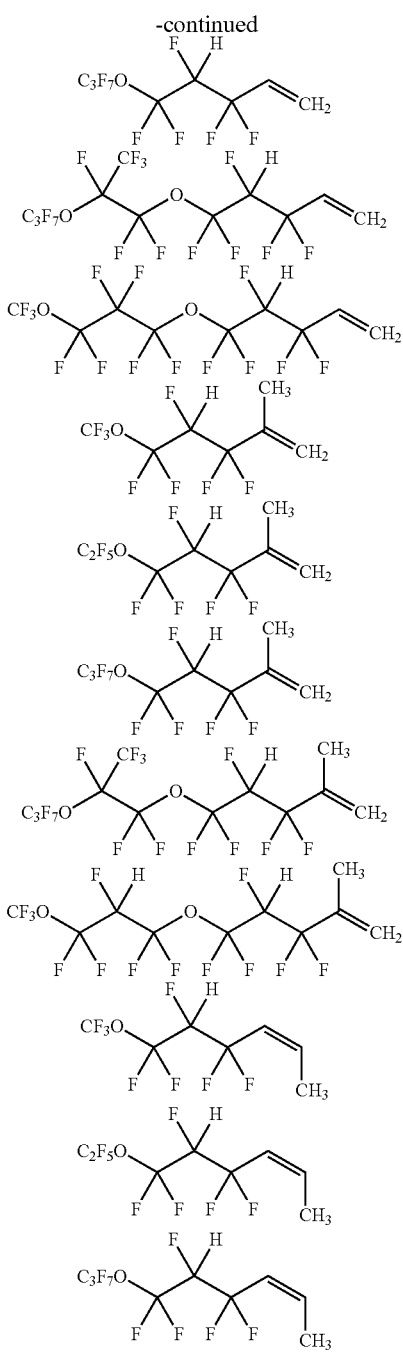

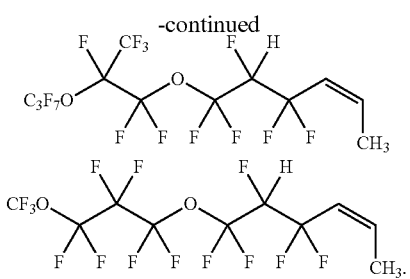

12. The unsaturated fluorinated compound of claim 1, wherein the unsaturated fluorinated compound has a degree of fluorination of at least 70%.

13. A composition comprising a purified form of the unsaturated fluorinated compound according to claim 1.

14. A working fluid comprising the unsaturated fluorinated compound according to claim 1, wherein the unsaturated fluorinated compound is present in the working fluid in an amount of at least 5% by weight based on the total weight of the working fluid.

15. A cleaning composition comprising the unsaturated fluorinated compound of claim 1.

16. An electrolyte solvent comprising the unsaturated fluorinated compound of claim 1.

17. A heat transfer fluid comprising the unsaturated fluorinated compound of claim 1.

18. A vapor phase soldering fluid comprising the unsaturated fluorinated compound of claim 1.

19. An apparatus for heat transfer comprising:
   a device; and
   a mechanism for transferring heat to or from the device, the mechanism comprising a heat transfer fluid that comprises the unsaturated fluorinated compound according to claim 1.

20. A method of making an unsaturated fluorinated compound, the method comprising:
   (i) reacting a perfluorinated allylic compound with a first alcohol in the presence of a free radical initiator to form a second alcohol, wherein the perfluorinated allylic compound comprises a perfluorinated allylic ether or a perfluorinated allylic amine, the first alcohol is a primary alcohol or a secondary alcohol, and the second alcohol is a secondary or tertiary fluorinated alcohol;
   (ii) acylating the second alcohol to form a fluorinated ester; and
   (iii) vapor phase dehydroacetoxylating the fluorinated ester to form the unsaturated fluorinated compound.

* * * * *

UNITED STATES PATENT AND TRADEMARK OFFICE
CERTIFICATE OF CORRECTION

PATENT NO. : 10,934,247 B2
APPLICATION NO. : 16/323623
DATED : March 2, 2021
INVENTOR(S) : Sean Smith et al.

Page 1 of 2

It is certified that error appears in the above-identified patent and that said Letters Patent is hereby corrected as shown below:

On the Title Page

Column 2 item (57), (Abstract)

Line 19, Below "soldering." insert -- 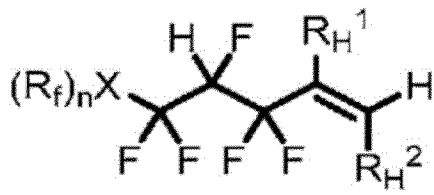 (I) --.

In the Specification

Column 8
Line 41, Delete "$a_1$" and insert -- $a_i$ --, therefor.

Column 11

Line 62-66 (Approx.), Delete " 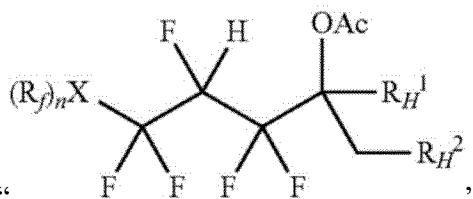 " and insert
-- 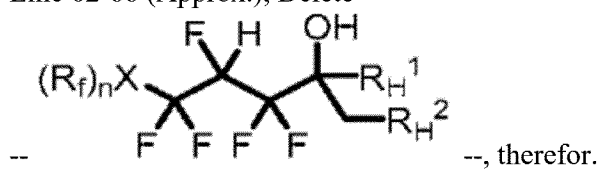 --, therefor.

Signed and Sealed this
Fifth Day of October, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,934,247 B2

Column 20
Line 57, After "(FSO$_2$)$_2$N–," insert -- BF$_4$–, --.

Column 21
Line 1, Delete "PF$_6$," and insert -- BF$_4$–, PF$_6$–, --, therefor.
Line 2, Delete "AsF$_6$)" and insert -- AsF$_6$–) --, therefor.